United States Patent

Egawa et al.

[11] Patent Number: 6,066,312
[45] Date of Patent: May 23, 2000

[54] TOPICAL COMPOSITION FOR APPLICATION TO THE SKIN CONTAINING AN ELLAGIC ACID-BASED COMPOUND OR SALT THEREOF

[75] Inventors: Makoto Egawa; Yukiko Marui, both of Tokyo, Japan

[73] Assignee: Lion Corporation, Japan

[21] Appl. No.: 08/893,648

[22] Filed: Jul. 11, 1997

[30] Foreign Application Priority Data

Jul. 16, 1996 [JP] Japan .................................. 8-205405

[51] Int. Cl.[7] ..................................................... A61K 7/48
[52] U.S. Cl. .......................... 424/62; 424/401; 424/489; 514/844
[58] Field of Search .................... 424/401, 489, 424/62; 514/844

[56] References Cited

U.S. PATENT DOCUMENTS 5,073,545  12/1991  Arima et al. .
5,141,741   8/1992  Ishida et al. .

*Primary Examiner*—Thurman K. Page
*Assistant Examiner*—Brian K. Seidleck
*Attorney, Agent, or Firm*—Lorusso & Loud

[57] ABSTRACT

A composition for external application having excellent percutaneous absorption property and skin-lightening and whitening effects, is disclosed, which composition comprises at least one particulate material selected from specific ellagic acid-based compound and an alkali metal salt of the ellagic acid-based compound, wherein the particulate material has an average particle diameter of not more than 50 $\mu$m and contains particles having a particle diameter of not more than 70 $\mu$m in an amount of not less than 70% by weight based on the weight of the particulate material.

8 Claims, 1 Drawing Sheet

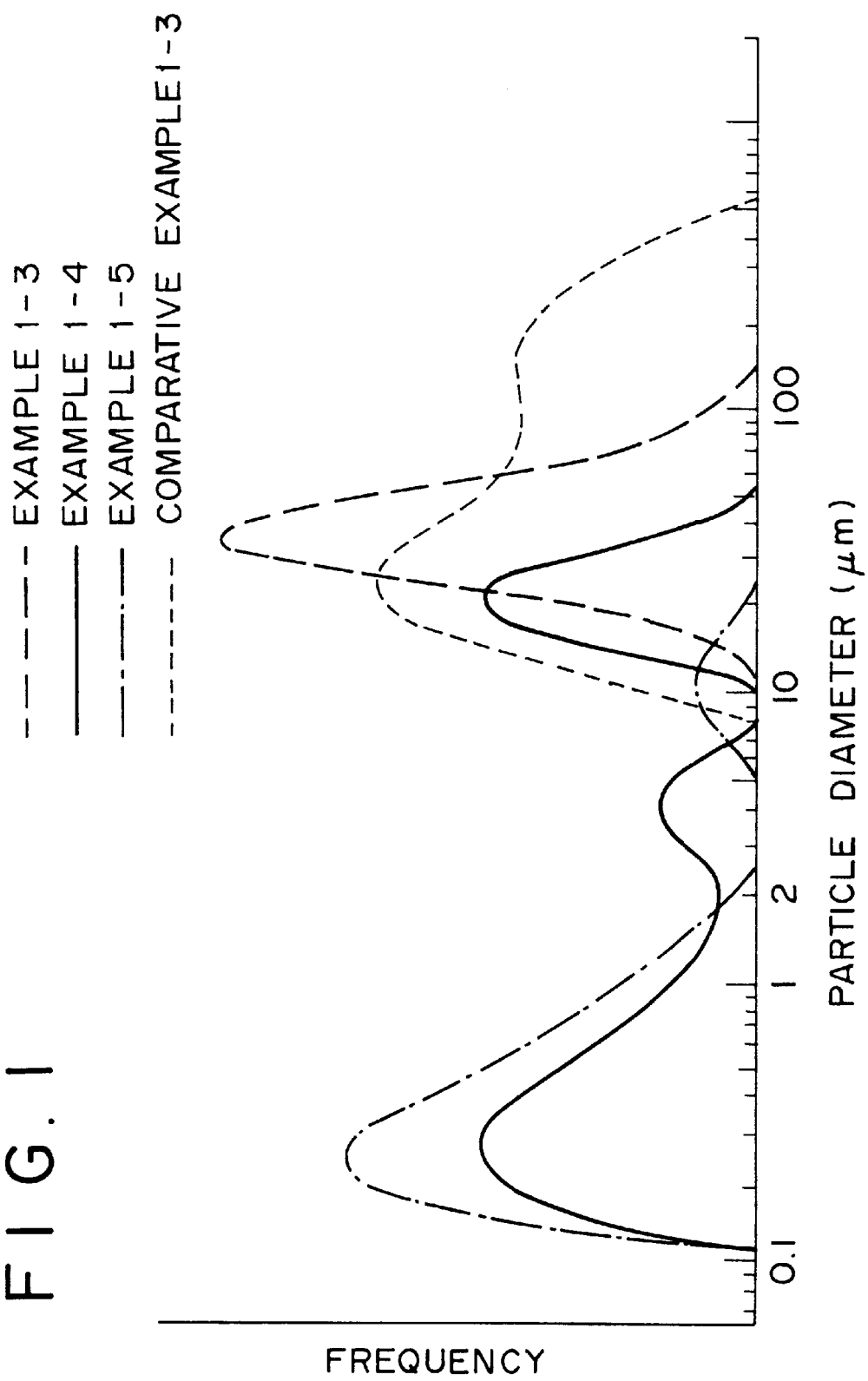

TOPICAL COMPOSITION FOR APPLICATION TO THE SKIN CONTAINING AN ELLAGIC ACID-BASED COMPOUND OR SALT THEREOF

BACKGROUND OF THE INVENTION

1. Field of the Invention

The present invention relates to a composition for external application having an excellent skin lightening and whitening effect.

2. Prior Art

Although there are many unclear points about development of pigmentation such as smear or freckle in human skin, it has been generally considered that stimulus due to hormone abnormality or UV radiation produces an excess amount of melanin, thereby causing undesired melanism in human skin.

In order to prevent or improve such a pigmentation, there have hitherto been used cosmetics having a lightening and whitening effect and containing, as effective components, peroxides such as hydrogen peroxide, zinc peroxide and magnesium peroxide, ascorbic acid, glutathione, colloidal sulfur, and various natural substances. However, many of these effective components has caused problems concerning safety, stability or smell. Besides, the effects of these components are not necessarily satisfactory.

Further, hydroquinone has been used as a skin-decoloring agent in U.S.A., etc. However, hydroquinone has irritating property and allergic property, thereby causing a problem concerning safety when the hydroquinone is used as effective component of cosmetics.

Accordingly, various studies has been made to develop cosmetics capable of exhibiting skin lightening and whitening effects without the afore-mentioned drawbacks. There have been proposed lightening and whitening agents for external application using kojic acid and kojic acid derivatives (Japanese Patent Unexamined Publication (KOKAI) No. 3538/1978, and Japanese Patent Examined Publications (KOKOKU) Nos. 18569/1981, 22151/1983, 9722/1985 and 60801/1986), cosmetics containing quercetin as effective components (Japanese Patent Unexamined Publication (KOKAI) No. 92305/1980), cosmetics containing fatty acid esters of quercetin as an effective component (Japanese Patent Unexamined Publication (KOKAI) No. 131911/1983), cosmetics containing catechin, etc., as effective components (Japanese Patent Unexamined Publication (KOKAI) No. 44375/1977), or the like. However, in practical use, these cosmetics have caused problems that the lightening and whitening components have still insufficient stability and therefore cannot exhibit a sufficient effect on human beings though their effects at the cell level are noticeable.

Under these circumstances, in order to provide agents for external application which are free from the afore-mentioned problems and excellent in skin lightening and whitening effect, and further do not cause problems concerning stability and smell, the present inventors have previously proposed the use of ellagic acid-based compounds or alkali metal salts of the ellagic acid-based compounds (Japanese Patent No. 1839986).

However, further studies made by the present inventors have revealed that in the case where the afore-mentioned ellagic acid-based compounds or alkali metal salts of the ellagic acid-based compounds are added into a base of cosmetics or quasi-drugs, the resultant agents have a low percutaneous absorption property and therefore cannot exhibit satisfactory effects even though these agents are blended at the concentration adopted for ordinary agents for external application.

SUMMARY OF THE INVENTION

It is therefore an object of the present invention to provide a composition for external application which contains as an effective component an ellagic acid-based compound or an alkali metal salt of the ellagic acid-based compound and are extremely excellent in percutaneous absorption.

As a result of intense studies made by the present inventors to overcome the afore-mentioned problems and improve the percutaneous absorption property of agents containing particles of the ellagic acid-based compound or the alkali salt thereof, it has been found that when the ellagic acid-based compound or the alkali metal salt thereof is finely pulverized into particles having an extremely small average particle diameter and a specific particle size distribution, it becomes possible to provide agents for external application having excellent properties. The present invention has been attained on the basis of this finding.

That is, in accordance with the present invention, there is provided a composition for external application, comprising at least one particulate material selected from the group consisting of (a) an ellagic acid-based compound of the general formula (I):

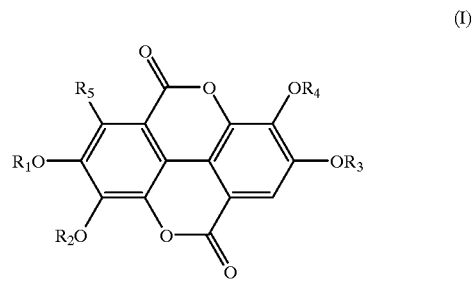

wherein $R^1$, $R^2$, $R^3$ and $R^4$ are the same or different and are independently hydrogen, an alkyl group having 1 to 20 carbon atoms, an acyl group having 1 to 20 carbon atoms, a polyoxyalkylene group of the formula: $-(C_mH_{2m}-O)_n-H$ where m is an integer of 2 or 3 and n is an integer of not less than 1, or a sugar residue of the formula (II):

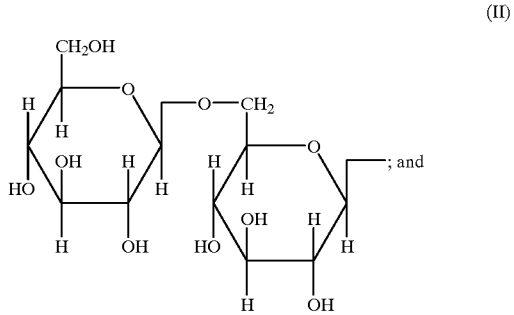

$R^5$ is hydrogen, a hydroxyl group or an alkoxy group having 1 to 8 carbon atoms, and (b) an alkali metal salt of the ellagic acid-based compound, wherein the particulate material having an average particle diameter of not more than 50 μm and containing particles having a particle diameter of not more than 70 μm in an amount of not less than 70% by weight based on the weight of the particulate material.

In general, in the case of particles, the amount of particles dissolved and the dissolving rate thereof are approximately in proportion to a surface area thereof in dissolving rate-determining step.

When applied to human skin, particulate ellagic acid-based compound or particulate alkali metal salt of the ellagic acid-based compound is first dissolved in water or lipid present thereon to form a solution, and then the solution penetrates through the skin, thereby exhibiting their effects.

In accordance with the present invention, it has been found that when the ellagic acid-based compound or the alkali metal salt thereof is finely pulverized and the finely pulverized material having a specific particle size distribution is incorporated as an effective component into a composition for external application, there can be obtained the following effects:

(1) The particles have a large surface area so that solubility and dissolving rate thereof is increased;
(2) The contact area of the particles with skin is increased;
(3) The rate of the composition penetrated into the skin and the amount thereof per unit time is increased;
(4) The percutaneous absorption of the composition is increased;
(5) The long-term stability of the composition is improved; and
(6) The feeling of use is excellent and the appearance of products is improved.

It is suggested that the afore-mentioned effects can be exhibited owing to such a relationship that in the case of extremely finely pulverized material, solubility thereof is in reverse proportion to particle diameter thereof due to the influence of surface energy.

Other objects and advantages of the present invention will become apparent from the following detailed description.

BRIEF DESCRIPTION OF THE DRAWING

FIG. 1 is a graph showing particle size distributions of sodium ellagate and ellagic acid used in Examples 1-3 to 1-5 and Comparative Example 1-3.

DETAILED DESCRIPTION OF THE INVENTION

The composition for external application according to the present invention contains, as an effective component, at least one particulate material selected from the group consisting of an ellagic acid-based compound of the afore-mentioned general formula (I) and an alkali metal salt of the ellagic acid-based compound.

The ellagic acid-based compound and the alkali metal salt thereof are described in detail below.

In the case where $R^1$, $R^2$, $R^3$ and $R^4$ in the general formula (I) are alkyl groups having 1 to 20 carbon atoms, specific examples of the alkyl groups may include a methyl group, an ethyl group, a propyl group or the like. Among them, preferred alkyl groups are methyl and ethyl.

In addition, in the case where $R^1$, $R^2$, $R^3$ and $R^4$ in the general formula (I) are acyl groups having 1 to 20 carbon atoms, specific examples of the acyl groups may include an acetyl group, a propionyl group or the like.

Further, in the case where $R^1$, $R^2$, $R^3$ and $R^4$ in the general formula (I) are polyoxyalkylene groups of the formula: —$(C_mH_{2m}—O)_n$—H, the polyoxyalkylene groups may be those in which n is an integer of not less than 1, e.g., a polyoxyethylene group, a polyoxypropylene group or the like. Among them, preferred polyoxyalkylene groups are those in which n is an integer of 5 to 40.

In any of the afore-mentioned cases, $R^1$, $R^2$, $R^3$ and $R^4$ in the general formula (I) may be the same or different.

Further, in the case where $R^5$ is an alkoxy group having 1 to 8 carbon atoms, specific examples of the alkoxy groups may include a methoxy group, an ethoxy group, a propoxy group or the like. Among them, the methoxy group is especially preferred.

Moreover, the alkali metal salts of ellagic acid-based compounds may include, for example, sodium salts, potassium salts or the like.

In the present invention, as the ellagic acid-based compounds, there can be suitably used substituted or unsubstituted ellagic acid which corresponds to a compound in which $R^1$, $R^2$, $R^3$, $R^4$ and $R^5$ in the general formula (I) all are hydrogen, or to a compound wherein $R^1$, $R^2$, $R^3$ and $R^4$ in the general formula (I) are hydrogen, a methyl group or an ethyl group and $R^5$ is hydrogen, a hydroxyl group or a methoxy group. Further, ellagic acids whose phenolic hydroxyl groups partially constitutes a sodium salt or a potassium salt are preferable, because such compounds can exhibit a high solubility.

When the ellagic acid-based compound or the alkali metal salt thereof is used to prepare a composition for external application, in order to impart lipophilic or hydrophilic nature to these compounds, an optional group selected from a long-chain alkyl group having up to 20 carbon atoms, a long-chain acyl group having up to 20 carbon atoms, a polyoxyalkylene group of the formula: —$(C_mH_{2m}—O)_n$—H where m is an integer of 2 or 3 and n is an integer of not less than 1, and a sugar residue of the afore-mentioned formula (II) may be substituted for some of $R^1$, $R^2$, $R^3$ and $R^4$ in the general formula (I). In addition, a long-chain alkoxy group having up to 8 carbon atoms may be substituted for $R^5$ in the general formula (I).

Specific examples of the afore-mentioned ellagic acid-based compounds and the alkali metal salts thereof may include ellagic acid, 3,4-di-o-methyl ellagic acid, 3,3'-di-o-methyl ellagic acid, 3,3', 4-tri-o-methyl ellagic acid, 3,3',4, 4'-tetra-o-methyl-5-methoxy ellagic acid, 3-o-ethyl-4-o-methyl-5-hydroxy ellagic acid, Amritoside which is a compound wherein RI in the general formula (I) is the sugar residue of the afore-mentioned formula (II) and $R^2$ to $R^5$ are hydrogen atoms, or alkali metal salts of these compounds.

The ellagic acid-based compounds can be readily obtained from natural substances such as *Eucalyptus cortex, Arctostaphylos uva-ursi folium, Granati cortex, Phyllanthus emblica fructus, Sapium sebiferum folium, Rhus chinensis folium, Acacia catechu, Platycarya strobilacea cortex, Ternunalia chebula cortex, Camptotheca acuminata radix, Polygonum bistorta rhizoma, Lagerstroemia subcostata folium, Sapium discolor rhizoma, Sapium discolor folium, Bischofia javanica radix, Lythrum salicaria herba, Geranium pratense rhizoma, Euphorbia hirta herba, Phyllanthus urinaria herba, Eucalyptus citriodora folium, Euphorbia royieana, Psidium guajava fructus, Psidium guajava cortex, Mangifera indica fructus, Cynips gallae tinctoriae, Syzygium cumini semen, Syzygium cumini cortex, Phyllanthus emblica radix, Phyllanthus emblica cortex, Phyllanthus emblica folium, Agrimonia pilosa radix, Psidium guajava folium, Sapium sebiferum cortex, Lagerstroemia indica radix, Phyllanthus urinaria herba* and *Geranium herba*, according to the below-mentioned method (refer to Japanese Patent Examined Publication (KOKOKU) No. 14605/1978).

That is, a dry pulverized product of the natural substance containing the ellagic acid-based compound is digested according to an ordinary method using acidic sulfite, and thereafter immersed in an aqueous alkaline solution of sodium hydroxide or sodium carbonate having a pH of 10 to 13. After the immersion solution is separated, acid such as sulfuric acid or acetic acid is added thereto to adjust the pH to 2 to 8, thereby obtaining a precipitate composed primarily of the ellagic acid-based compound. The precipitate is centrifuged to collect coarse ellagic acid-based compound, which is then rinsed in water to remove impurities therefrom, thereby preparing an ellagic acid-based compound having a high purity.

Thus, the ellagic acid-based compound used for the production of the composition for external application according to the present invention is extensively present in natural substances and therefore considered to exhibit an extremely high safety. When the compound was tested to assure its safety, it has not posed any serious problem concerning acute toxicity, skin-irritating property, skin-sensitizing property and mutagenic property. This indicates that the ellagic acid-based compound can be practically used with a high safety.

In the present invention, the ellagic acid-based compounds and the alkali metal salts of the ellagic acid-based compounds can be used singly or in the form of any two or more thereof.

The amount of the ellagic acid-based compound or the alkali metal salt thereof contained in the composition for external application is preferably in the range of 0.001 to 30% by weight, more preferably 0.05 to 10% by weight, based on the total weight of the composition.

In the following, there are described particle diameter and particle size distribution of the ellagic acid-based compound and the alkali metal salt thereof used in the composition for external application according to the present invention.

The ellagic acid-based compound or alkali metal salt thereof used in the form of particles has an average particle diameter of not more than 50 $\mu$m and contains particles having a particle diameter of not more than 70 $\mu$m in an amount of not less than 70% by weight based on the total weight thereof. The particulate ellagic acid-based compound or the particulate alkali metal salt of the ellagic acid-based compound has preferably an average particle diameter of not more than 10 $\mu$m and contains particles having a particle diameter of not more than 30 $\mu$m in an amount of not less than 70% by weight based on the total weight thereof. More preferably, the particulate ellagic acid-based compound or the particulate alkali metal salt of the ellagic acid-based compound has an average particle diameter of not more than 1 $\mu$m and contains particles having a particle diameter of not more than 3 $\mu$m in an amount of not less than 70% by weight based on the total weight thereof.

The particulate ellagic acid-based compound or alkali metal salt thereof having the afore-mentioned particular average diameter and particle size distribution can be prepared by ordinary pulverizing methods. As the ordinary pulverizing methods, there may be exemplified dry methods using pulverizers such as a colloid mill, a ball mill or a jet mill, and wet methods using an ultrasonic pulverizer or a high-speed shearing apparatus such as a homomixer, CLEARMIX manufactured by M. TECHNIQUE Co., Ltd. or MILDER manufactured by EBARA SEISAKUSHO Co., Ltd.

The specific method for pulverizing the ellagic acid-based compound or the alkali metal salt thereof is described below.

The ellagic acid-based compound or its alkali metal salt is first dispersed in water, an aqueous solution or other solvents which can be maintained in a liquid state at a normal temperature and may have particular solutes. The ellagic acid-based compound or its alkali metal salt in the dispersion is pulverized for a predetermined period of time so as to adjust the particle diameters thereof into desired ones. The particle diameters can be controlled by varying the treating time.

For example, in the case where it is intended to obtain the particulate material having an average particle diameter of not more than 50 $\mu$m and containing particles having a particle diameter of not more than 70 $\mu$m in an amount of not less than 70% by weight, the pulverization is conducted by a colloid mill for 1 to 5 minutes. In addition, in the case where it is intended to obtain the particulate material having an average particle diameter of not more than 10 $\mu$m and containing particles having a particle diameter of not more than 30 $\mu$m in an amount of not less than 70% by weight, the pulverization is conducted by using an ultrasonic wave for 5 to 10 minutes. Further, in the case where it is intended to obtain the particulate material having an average particle diameter of not more than 1 $\mu$m and containing particles having a particle diameter of not more than 3 $\mu$m in an amount of not less than 70% by weight, the pulverization is conducted by CLEARMIX for 20 to 30 minutes. These treating times are appropriately adjusted depending upon the amount of the ellagic acid-based compound or its alkali metal salt to be treated.

Alternatively, the particulate ellagic acid-based compound or alkali metal salt thereof having the afore-mentioned particular average particle diameters and particle size distributions can also be obtained by crystallization. In this case, the ellagic acid-based compound or the alkali metal salt thereof is first dissolved in an aqueous solution containing alkali metal hydroxide in such a particular concentration that the solution has a pH of 12 to 14. Thereafter, acid (i.e., any inorganic or organic acid, preferably sulfuric acid in view of the post-treatment) is added to the aqueous solution to adjust the pH thereof to 2 to 8 while vigorously stirring, thereby crystallizing the ellagic acid-based compound or the alkali metal salt thereof to form a particulate material having the afore-mentioned particular average particle diameter and particle size distribution.

Also, if required, various additives ordinarily used in agents for external application, for example, oils, water, surfactants, humectants, alcohols, thickeners, anti-oxidants, sequestrants, pH adjusters, preservatives, perfumes, pigments, ultraviolet light absorbers, ultraviolet light scattering agents, vitamins, amino acids or the like can be blended in the composition according to the present invention, unless peculiar effects of the present invention is adversely affected by the addition thereof.

EXAMPLES

The present invention will be described in more detail by way of examples. However, these examples are only illustrative and not intended to limit the scope of the present invention.

First, typical processes for the production of finely pulverized ellagic acid-based compounds and alkali metal salts thereof are described by way of Preparation Examples.

Preparation Example 1 (Ultrasonic method)

Ellagic acid was added to purified water to prepare a dispersion containing 2.5% ellagic acid. One kilogram of the dispersion was treated by using an ultrasonic pulverizer for one minute to obtain a particulate material having an average particle diameter of 60 $\mu$m and containing particles having a particle diameter of not more than 70 μm in an amount of 75% by weight. In addition, the same procedure as described above was repeated except that the treatment by the ultrasonic pulverizer was carried out for 3 minutes, so that a particulate material having an average particle diameter of 50 μm and containing particles having a particle diameter of not more than 70 μm in an amount of 62% by weight could be obtained. Further, the same procedure as described above was repeated except that the treatment by the ultrasonic pulverizer was carried out for 8 minutes, so that a particulate material having an average particle diameter of 8 μm and containing particles having a particle diameter of not more than 30 μm in an amount of 75% by weight could be obtained. Furthermore, the same procedure as described above was repeated except that the treatment by the ultrasonic pulverizer was carried out for 20 minutes, so that a particulate material having an average particle diameter of 0.5 μm and containing particles having a particle diameter of not more than 3 μm in an amount of 74% by weight could be obtained.

Preparation Example 2 (CLEARMIX method)

Ellagic acid salt was added to purified water to prepare a dispersion containing 2.5% ellagic acid salt. One kilogram of the dispersion was treated by using CLEARMIX for 0.5 minute to obtain a particulate material having an average particle diameter of 60 μm and containing particles having a particle diameter of not more than 70 μm in an amount of 75% by weight. In addition, the same procedure as described above was repeated except that the treatment by the CLEARMIX was carried out for 1 minute, so that a particulate material having an average particle diameter of 50 μm and containing particles having a particle diameter of not more than 70 μm in an amount of 58% by weight could be obtained. Further, the same procedure as described above was repeated except that the treatment by the CLEARMIX was carried out for 3 minutes, so that a particulate material having an average particle diameter of 40 μm and containing particles having a particle diameter of not more than 70 μm in an amount of 92% by weight could be obtained. Further, the same procedure as described above was repeated except that the treatment by the CLEARMIX was carried out for 5 minutes, so that a particulate material having an average particle diameter of 0.7 μm and containing particles having a particle diameter of not more than 30 μm in an amount of 95% by weight could be obtained. Further, the same procedure as described above was repeated except that the treatment by the CLEARMIX was carried out for 20 minutes, so that a particulate material having an average particle diameter of 0.5 μm and containing particles having a particle diameter of not more than 3 μm in an amount of 70% by weight could be obtained. Furthermore, the same procedure as described above was repeated except that the treatment by the CLEARMIX was carried out for 60 minutes, so that a particulate material having an average particle diameter of 0.2 μm and containing particles having a particle diameter of not more than 3 μm in an amount of 99% by weight could be obtained.

Preparation Example 3 (colloid mill method)

3,3'-di-o-methyl ellagic acid was added to purified water to prepare a dispersion containing 2.5% of 3,3'-di-o-methyl ellagic acid. One kilogram of the dispersion was treated by using a colloid mill for 0.3 minute to obtain a particulate material having an average particle diameter of 60 μm and containing particles having a particle diameter of not more than 70 μm in an amount of 75% by weight. In addition, the same procedure as described above was repeated except that the treatment by the colloid mill was carried out for 0.5 minute, so that a particulate material having an average particle diameter of 40 μm and containing particles having a particle diameter of not more than 70 μm in an amount of 67% by weight could be obtained. Further, the same procedure as described above was repeated except that the treatment by the colloid mill was carried out for 3 minutes, so that a particulate material having an average particle diameter of 8 μm and containing particles having a particle diameter of not more than 30 μm in an amount of 75% by weight could be obtained. Furthermore, the same procedure as described above was repeated except that the treatment by the colloid mill was carried out for 40 minutes, so that a particulate material having an average particle diameter of 0.6 μm and containing particles having a particle diameter of not more than 1 μm in an amount of 75% by weight could be obtained.

Preparation Example 4 (MILDER method)

Ellagic acid was added to purified water to prepare a dispersion containing 2.5% ellagic acid. One kilogram of the dispersion was treated by using MILDER for 2 minutes to obtain a particulate material having an average particle diameter of 60 μm and containing particles having a particle diameter of not more than 70 μm in an amount of 75% by weight. In addition, the same procedure as described above was repeated except that the treatment by the MILDER was carried out for 5 minute, so that a particulate material having an average particle diameter of 30 μm and containing particles having a particle diameter of not more than 70 μm in an amount of 62% by weight could be obtained. Further, the same procedure as described above was repeated except that the treatment by the MILDER was carried out for 10 minutes, so that a particulate material having an average particle diameter of 9 μm and containing particles having a particle diameter of not more than 30 μm in an amount of 75% by weight could be obtained. Furthermore, the same procedure as described above was repeated except that the treatment by the MILDER was carried out for 40 minutes, so that a particulate material having an average particle diameter of 0.8 μm and containing particles having a particle diameter of not more than 30 μm in an amount of 97% by weight could be obtained.

Preparation Example 5 (homomixer method)

Ellagic acid was added to purified water to prepare a dispersion containing 2.5% ellagic acid. One kilogram of the dispersion was treated by using a homomixer for 20 minute to obtain a particulate material having an average particle diameter of 8 μm and containing particles having a particle diameter of not more than 30 μm in an amount of 75% by weight.

Preparation Example 6 (crystallization method)

20 g of commercially available ellagic acid having an average particle diameter of 150 μm and manufactured by TOKYO KASEI KOGYO Co., Ltd., was dispersed in 500 of purified water while stirring. Thereafter, 500 g of 1N sodium hydroxide aqueous solution was added to the dispersion to dissolve the ellagic acid therein. While vigorously stirring the resultant solution, 6N sulfuric acid solution was slowly dropped thereinto at a rate of 1 ml/min until the pH of the solution reached 2. The resultant precipitate was removed from the solution by centrifugal separation, and then rinsed in water two times, followed by drying. As a result, there was obtained 18.2 g of particulate ellagic acid having an average particle diameter of 0.2 μm and containing particles having a particle diameter of not more than 1 μm in an amount of 98% by weight.

Examples 1-1 to 1-10 and Comparative Examples 1-1 to 1-12

The percutaneous absorption is known as an important factor to evaluate performance of medicinal substances in biological applications thereof. From this viewpoint, in Examples 1-1 to 1-10 and Comparative Examples 1-1 to 1-12, various ellagic acid-based compounds and alkali metal salts thereof having a variety of particle diameters were tested to measure amounts of percutaneous absorption of these compounds in vitro. The measured values were compared to assure difference in amount of percutaneous absorption therebetween due to particle diameters thereof.

Specifically, a skin specimen was cut from a back of a guinea pig (Std: Hartley-series; male) and fixedly interposed between a donor and a receptor of a cell for percutaneous absorption test. Next, after the receptor of the cell was filled with sterilized physiological saline, the cell was immersed in a water tank to conduct the incubation at 30° C. while stirring. Successively, 50 mg of each of compositions shown in FIG. 1 was applied to a donor-side surface of the skin. Incidentally, ellagic acid-based compounds or alkali metal salts thereof used above were homogeneously mixed with 10% radioisotopic substance thereof labeled with $^{14}$C. The mixture was used as it were or after having been pulverized into fine particles under the conditions as shown in Table 1 (as described in detail in the above Preparation Examples).

Meanwhile, the particle size distributions of sodium ellagate and ellagic acid used in Examples 1-3 to 1-5 and Comparative Example 1-3 are shown in FIG. 1.

After completion of 24 hour-incubation, 1 ml of receptor liquid was sampled. Three milliliters of Pico-Fluor 40 (trade mark) manufactured by Packard Japan Co., Ltd., was added to the receptor liquid and then the radioactivity of the mixed solution was measured by a liquid scintillation counter to determine the amount of the ellagic acid-based compound or the alkali metal salt thereof which has penetrated through the skin. After unabsorbed composition adhered to the skin was washed off, a small piece having a predetermined area was cut from the skin by a punch having a diameter of 1 cm. The small piece of skin was further cut into chips by scissors so as to facilitate dissolution thereof into liquid, and then charged into a glass vial for liquid scintillation. 2 ml of Soluene®-350 manufactured by Packard Japan Co., Ltd., was charged into the glass vial and heated to 60° C. to dissolve the skin chips therein. After completion of the dissolution, 20 ml of Hionic-Fluor was added to the solution and then the radioactivity of the mixed solution was measured by the liquid scintillation counter to determine amounts of the ellagic acid-based compound or the alkali metal salt thereof contained in the skin. The sum of the thus-measured amounts of the ellagic acid-based compound or the alkali metal salt thereof penetrating through the skin and contained in the skin was defined as the amount of percutaneous absorption of these compounds. Based on the amounts obtained, the percutaneous absorption properties of a variety of ellagic acid-based compounds and alkali metal salts thereof were evaluated. The results are shown in Table 1.

Incidentally, in Table 1, the amounts of percutaneous absorption of the ellagic acid-based compounds or the alkali metal salts thereof are indicated by relative values to the amount of percutaneous absorption of non-pulverized ellagic acid-based compound or non-pulverized alkali metal salt thereof when the latter amount is regarded as a value of 1. Further, the amounts of components blended in each composition are represented by "% by weight".

Respective components used in Examples and Comparative Examples are shown below.

| Components | Amount to be blended(wt. %) |
|---|---|
| "A" component (compounds, amounts and average particle diameters thereof are shown in TABLE 1) | |
| 1,3-butylene glycol | 5.0 |
| Glycerol | 5.0 |
| Ethanol | 8.0 |
| Xanthane gum | 0.3 |
| Purified water | Balance |

TABLE 1

| | (A) component | Amount blended (%) | Average particle diameter (μm) (particle size distribution) | Pulverizing method | Treating time (min) | Amount of percutaneous absorption (relative value) |
|---|---|---|---|---|---|---|
| Comparative Example 1-1 | Ellagic acid | 0.5 | 100 | Untreated | 0 | 1 |
| Comparative Example 1-2 | Ellagic acid | 0.5 | 60 (75 wt % of not more than 70 μm) | Ultrasonic | 1 | 1.5 |
| Comparative Example 1-3 | Ellagic acid | 0.5 | 50 (62 wt % of not more than 70 μm) | Ultrasonic | 3 | 1.8 |
| Example 1-1 | Ellagic acid | 0.5 | 8 (75 wt % of not more than 30 μm) | Ultrasonic | 8 | 5 |
| Example 1-2 | Ellagic acid | 0.5 | 0.5 (74 wt % of not more than 3 μm) | Ultrasonic | 20 | 10 |
| Comparative Example 1-4 | Sodium ellagate | 0.3 | 60 | Untreated | 0 | 1 |
| Comparative Example 1-5 | Sodium ellagate | 0.3 | 60 (75 wt % of not more than 70 μm) | CLEAR-MIX | 0.5 | 1.8 |
| Comparative Example 1-6 | Sodium ellagate | 0.3 | 50 (58 wt % of not more than 70 μm) | CLEAR-MIX | 1 | 2.5 |

TABLE 1-continued

| | (A) component | Amount blended (%) | Average particle diameter (μm) (particle size distribution) | Pulverizing method | Treating time (min) | Amount of percutaneous absorption (relative value) |
|---|---|---|---|---|---|---|
| Example 1-3 | Sodium ellagate | 0.3 | 40 (92 wt % of not more than 70 μm) | CLEAR-MIX | 3 | 3 |
| Example 1-4 | Sodium ellagate | 0.3 | 0.7 (95 wt % of not more than 30 μm) | CLEAR-MIX | 5 | 7 |
| Example 1-5 | Sodium ellagate | 0.3 | 0.5 (70 wt % of not more than 3 μm) | CLEAR-MIX | 20 | 10 |
| Example 1-6 | Sodium ellagate | 0.3 | 0.2 (99 wt % of not more than 3 μm) | CLEAR-MIX | 60 | 15 |
| Comparative Example 1-7 | 3,3'-di--o-methyl ellagic acid | 0.2 | 80 | Untreated | 0 | 1 |
| Comparative Example 1-8 | 3,3'-di--o methyl ellagic acid | 0.2 | 60 (75 wt % of not more than 70 μm) | Colloid mill | 0.3 | 1.5 |
| Comparative Example 1-9 | 3,3'-di--o-methyl ellagic acid | 0.2 | 40 (67 wt % of not more than 70 μm) | Colloid mill | 0.5 | 2.7 |
| Example 1-7 | 3,3'-di--o-methyl ellagic acid | 0.2 | 8 (75 wt % of not more than 30 μm) | Colloid mill | 3 | 5 |
| Example 1-8 | 3,3'-di--o-methyl ellagic acid | 0.2 | 0.6 (75 wt % of not more than 1 μm) | Colloid mill | 40 | 8 |
| Comparative Example 1-10 | Ellagic acid | 3.0 | 120 | Untreated | 0 | 1 |
| Comparative Example 1-11 | Ellagic acid | 3.0 | 60 (75 wt % of not more than 70 μm) | MILDER | 2 | 1.8 |
| Comparative Example 1-12 | Ellagic acid | 3.0 | 30 (62 wt % of not more than 70 μm) | MILDER | 5 | 2.8 |
| Example 1-9 | Ellagic acid | 3.0 | 9 (75 wt % of not more than 30 μm) | MILDER | 10 | 4 |
| Example 1-10 | Ellagic acid | 3.0 | 0.8 (97 wt % of not more than 30 μm) | MILDER | 40 | 5 |

As is appreciated from Table 1, the ellagic acid-based compounds or the alkali metal salts thereof having an average particle diameter of not more than 50 μm and containing particles having a particle diameter of not more than 70 μm in an amount of not less than 70% by weight exhibited a considerably improved percutaneous absorption property. Further, it was confirmed that the percutaneous absorption properties of the acid-based compounds or the alkali metal salts thereof having an average particle diameter of not more than 10 μm and containing particles having a particle diameter of not more than 30 μm in an amount of not less than 70% by weight were more excellent than those of the afore-mentioned compounds. Furthermore, it was confirmed that the ellagic acid-based compounds or the alkali metal salts thereof having an average particle diameter of not more than 1 μm and containing particles having a particle diameter of not more than 3 μm in an amount of not less than 70% by weight exhibited most excellent percutaneous absorption property.

Examples 2-1 to 2-2 and Comparative Examples 2-1 to 2-4

Oil phase components and aqueous phase components shown in Table 2 were separately dissolved while heating at 70° C. The resultant solutions separately prepared were mixed together while stirring to form an emulsion. The emulsion was cooled to room temperature to prepare cosmetic creams as shown in FIG. 2. Incidentally, in Table 3, the amounts of respective components blended are represented by "% by weight".

TABLE 2

| | Examples | | Comparative Examples | | | |
|---|---|---|---|---|---|---|
| Component | 2-1 | 2-2 | 2-1 | 2-2 | 2-3 | 2-4 |
| Ellagic acid (CLEARMIX pulverization for 3 min.; average particle diameter: 40 μm, 92 wt % of 70 μm or less) | 0.3 | — | — | — | — | — |
| Ellagic acid (ultrasonic pulverization for 3 min.; average particle diameter: 50 μm; 62 wt % of 70 μm or less) | — | — | — | — | 0.3 | — |
| Ellagic acid (no pulverization; | — | — | 0.3 | — | — | — |

TABLE 2-continued

|  | Examples | | Comparative Examples | | | |
| --- | --- | --- | --- | --- | --- | --- |
| Component | 2-1 | 2-2 | 2-1 | 2-2 | 2-3 | 2-4 |
| average particle diameter: 100 μm) | | | | | | |
| Potassium ellagate (MILDER pulverization for 40 min; average particle diameter: 0.8 μm; 97 wt % of 30 μm or less) | — | 1.0 | — | — | — | — |
| Potassium ellagate (no pulverization; average particle diameter: 80 μm) | — | — | — | 1.0 | — | — |
| Lanolin | 2.0 | 2.0 | 2.0 | 2.0 | 2.0 | 2.0 |
| Sorbitan mono-stearate | 2.0 | 2.0 | 2.0 | 2.0 | 2.0 | 2.0 |
| Polyoxyehtylene-sorbitan mono-palmitate | 2.0 | 2.0 | 2.0 | 2.0 | 2.0 | 2.0 |
| Beeswax | 5.0 | 5.0 | 5.0 | 5.0 | 5.0 | 5.0 |
| Squalane | 10.0 | 10.0 | 10.0 | 10.0 | 10.0 | 10.0 |
| Liquid paraffin | 15.0 | 15.0 | 15.0 | 15.0 | 15.0 | 15.0 |
| Propylene glycol | 3.0 | 3.0 | 3.0 | 3.0 | 3.0 | 3.0 |
| 2-ethylhexyl p-methoxy-cinnamate | 0.8 | 0.8 | 0.8 | 0.8 | 0.8 | 0.8 |
| 4-tert-butyl-4'-methoxy-benzoyl-methane | 0.3 | 0.3 | 0.3 | 0.3 | 0.3 | 0.3 |
| dipropylene-glycol | 7.0 | 7.0 | 7.0 | 7.0 | 7.0 | 7.0 |
| Methylparaben | 0.2 | 0.2 | 0.2 | 0.2 | 0.2 | 0.2 |
| Purified water | | | Balance | | | |

The effectiveness of the thus-prepared cosmetic creams was evaluated as follows.

That is, The hair on the backs of colored guinea pigs (Cavia porcellus; each group consisting of 6 animals) were sheared, and the naked backs of the guinea pigs were respectively irradiated with UV-B (ultraviolet ray) of ½ MED amount four times a day. After the pigmentation was caused on the backs, the cosmetic creams were coated onto the skin area of about 4 cm² on the respective backs in an amount of 0.25 g each, four times a day for 4 weeks. The change in skin color was determined by measuring the L-value (lightness) thereof by a color-difference meter. Incidentally, the larger L-value represents a higher whitening of the skin. Further, the appearance of the respective cosmetic creams coated was evaluated by the following tests and ratings. The results are shown in Table 3.

Tests for Evaluation of Appearance of Creams Coated:

0.08 g of each cosmetic cream was applied onto a black flockpaper having a size of 10 cm×10 cm (100 cm²) and extended into a thin layer thereover. The appearances of the respective thus-applied cosmetic creams were visually observed to determine whether or not any particles of ellagic acid or potassium ellagate was recognized.

Evaluation Ratings:

A: Not recognized at all;
B: Slightly recognized; and
C: Remarkably recognized.

TABLE 3

|  | L-value (average value: n = 6) | | Appearance |
| --- | --- | --- | --- |
|  | Before test | After test | upon coating |
| Example 2-1 | 35.5 | 49.0 | A |
| Example 2-2 | 35.8 | 48.5 | A |
| Comparative Example 2-1 | 35.7 | 41.5 | C |
| Comparative Example 2-2 | 35.8 | 40.9 | C |
| Comparative Example 2-3 | 35.6 | 38.5 | B |
| Comparative Example 2-4 | 35.5 | 36.1 | — |

As is appreciated from Table 3, the cream compositions of Examples 2-1 and 2-2 according to the present invention in which the ellagic acid and the alkali metal salt thereof having an average particle diameter of not more than 50 μm and containing particles having a particle diameter of not more than 70 μm in an amount of not less than 92% by weight were used, exhibited more remarkable effect for discoloring the pigmentation of colored guinea pigs, as compared to those compositions of Comparative Examples 2-1 to 2-4 containing non-pulverized or insufficiently pulverized ellagic acids or alkali metal salts. This indicates that these compositions can exhibit more remarkable lightening and whitening effects.

In addition, the compositions according to the present invention are more excellent in appearance upon coating than those of Comparative Examples.

Example 3 and Comparative Examples 3-1 and 3-2

Oil phase components and aqueous phase components shown in Table 4 were separately heated at 70° C. to prepare solutions. The resultant solutions separately prepared were mixed together while stirring to form an emulsion. The emulsion was cooled to room temperature, during which perfume was added to the emulsion, to prepare cosmetic milky lotions. Incidentally, in Table 4, the amounts of respective components blended are represented by "% by weight".

TABLE 4

| Component | Example 3 | Comparative Example 3-1 | Comparative Example 3-2 |
|---|---|---|---|
| Ellagic acid (CLEARMIX pulverization for 20 min.; average particle diameter: 0.5 μm, 70 wt % of 3 μm or less) | 1.0 | — | — |
| Ellagic acid (colloid mill pulverization for 0.5 min.; average particle diameter: 40 μm; 62 wt % of 70 μm or less) | — | 1.0 | — |
| Ellagic acid (no pulverization; average particle diameter: 120 μm) | — | — | 1.0 |
| Squalane | 5.0 | 5.0 | 5.0 |
| Isopropyl palmitate | 2.0 | 2.0 | 2.0 |
| Cetostearyl alcohol | 1.2 | 1.2 | 1.2 |
| Glycerol mono-stearate | 1.3 | 1.3 | 1.3 |
| Polyethylene glycol mono-stearate | 1.5 | 1.5 | 1.5 |
| Propylene glycol | 5.0 | 5.0 | 5.0 |
| Carboxy-vinyl polymer | 0.1 | 0.1 | 0.1 |
| Tri-isopropanol amine | 0.1 | 0.1 | 0.1 |
| Stearyl glycyrrhetate | 0.2 | 0.2 | 0.2 |
| Tocopherol acetate | 0.2 | 0.2 | 0.2 |
| Methylparaben | 0.2 | 0.2 | 0.2 |
| Purified water | Balance | Balance | Balance |
| Perfume | Trace | Trace | Trace |

The effectiveness of the thus-prepared cosmetic milky lotions were evaluated by the following method and ratings.

That is, the milky lotions prepared in the above Example 3 and Comparative Examples 3-1 and 3-2 were coated onto pigment-depositing portions on the skin of 15 persons of different sexes twice a day for 5 weeks. After 5 weeks, the pigment-depositing portions were observed to determine lightening and whitening effects of the products. The results are shown in Table 5.

Incidentally, the evaluation of lightening and whitening effects was made according to the following ratings.

(1) Remarkably effective: Substantially no pigmentation was noticeable;
(2) Effective: Extremely slight pigmentation was noticeable;
(3) Slightly effective: Pigmentation was slightly reduced; and
(4) Ineffective: No change in pigmentation occurred.

In addition, the appearance of the milky lotions upon coating was evaluated in the same manner as in Examples 2.

TABLE 5

| Results | Lightening and whitening effects | | | | Appearance upon coating |
|---|---|---|---|---|---|
| | Remarkably effective | Effective | Slightly Effective | Ineffective | |
| Example 3 | 5 | 5 | 4 | 1 | A |
| Comparative Example 3-1 | 0 | 5 | 7 | 3 | B |
| Comparative Example 3-2 | 0 | 4 | 6 | 5 | C |

As is appreciated from Table 5, the milky lotion compositions of Example 3 according to the present invention in which the ellagic acid having an average particle diameter of 0.5 μm and containing particles having a particle diameter of not more than 3 μm in an amount of 70% by weight was used, had more remarkable lightening and whitening effects, as compared to those compositions of Comparative Examples 3-1 and 3-2 containing non-pulverized or insufficiently pulverized ellagic acid. During and after the 5-week use of the composition according to the present invention, there was no abnormality on the skin to which the composition was applied.

In addition, the composition according to the present invention was more excellent in appearance upon coating than those of Comparative Examples.

Example 4 and Comparative Example 4

Components shown in Table 6 were mixed together to prepare toilet water. Incidentally, in Table 6, the amounts of respective components blended are represented by "% by weight".

TABLE 6

| Component | Example 4 | Comparative Example 4 |
|---|---|---|
| Sodium ellagate (treated to pH 5, ultrasonic pulverization for 8 min.; average particle diameter: 8 μm, 75 wt % of 30 μm or less) | 1.5 | — |
| Sodium ellagate (treated to pH 5, no pulverization; average particle diameter: 100 μm) | — | 1.5 |
| Glycerol | 4.0 | 4.0 |
| Ethanol | 8.0 | 8.0 |
| Carboxy-vinyl polymer | 0.2 | 0.2 |
| Triethanol amine | 0.12 | 0.12 |
| Purified water | Balance | Balance |

The effectiveness of the thus-prepared toilet water was evaluated in the same manner as in Example 3 except that the test period was prolonged to 6 weeks. In addition, the appearance of the products upon coating was evaluated in the same manner as in Examples 2. The results are shown in Table 7.

TABLE 7

| Results | Lightening and whitening effects | | | | Appearance upon coating |
|---|---|---|---|---|---|
| | Remarkably effective | Effective | Slightly Effective | Ineffective | |
| Example 4 | 5 | 5 | 4 | 1 | A |
| Comparative Example 4 | 1 | 3 | 6 | 5 | C |

As is appreciated from Table 7, the toilet water composition of Example 4 according to the present invention in which sodium ellagate having an average particle diameter of 8 μm and containing particles having a particle diameter of not more than 30 μm in an amount of 75% by weight was used, had more remarkable lightening and whitening effects, as compared to the composition of Comparative Example 4 containing non-pulverized sodium ellagate. During and after the 6-week use of the composition according to the present invention, there was caused no abnormality on the skin to which the composition was applied.

In addition, the composition according to the present invention was more excellent in appearance upon coating than that of Comparative Example.

Example 5 and Comparative Example 5

Components shown in Table 8 were mixed together to prepare cosmetic packs as shown in Table 8. Incidentally, in Table 6, the amounts of respective components blended are represented by "% by weight". Ellagic acid for the pack according to the present invention was prepared by crystallization method as follows.

Preparation of Ellagic Acid:

20 g of commercially available ellagic acid having an average particle diameter of 150 μm and manufactured by TOKYO KASEI KOGYO Co., Ltd., was dispersed in 500 g of purified water while stirring. Thereafter, 500 g of 1N sodium hydroxide aqueous solution was added to the dispersion to dissolve the ellagic acid therein. While vigorously stirring the resultant solution by a paddle, 6N sulfuric acid solution was slowly dropped thereinto at a rate of 1 ml/min until the pH of the solution reached 2. The resultant precipitate was removed from the solution by centrifugal separation, and then rinsed in water two times, followed by drying. As a result, there was obtained 18.2 g of particulate ellagic acid having an average particle diameter of 0.2 μm and containing particles having a particle diameter of not more than 1 μm in an amount of 98% by weight.

TABLE 8

| Component | Example 5 | Comparative Example 5 |
| --- | --- | --- |
| Ethyl alcohol phase components | | |
| Ethyl alcohol | 10.0 | 10.0 |
| Polyvinyl alcohol | 15.0 | 15.0 |
| Glycerol | 2.5 | 2.5 |
| Methylparaben | 0.15 | 0.15 |
| Butylparaben | 0.05 | 0.05 |
| Di-potassium glycyrrhetate | 0.2 | 0.2 |
| Aqueous phase components | | |
| Ellagic acid (crystallization; average particle diameter: 0.2 μm, 98 wt % of 1 μm or less) | 0.2 | — |
| Ellagic acid (no pulverization; average particle diameter: 150 μm) | — | 0.2 |
| Sodium carboxymethylcellulose | 3.0 | 3.0 |
| POE(15)-Oleyl ether | 1.0 | 1.0 |
| Purified water | Balance | Balance |
| Perfume | Adequate amount | Adequate amount |

The effectiveness of the thus-prepared cosmetic packs were evaluated by the following method.

That is, the cosmetic packs were coated onto pigment depositing portions on the skin of 10 persons of different sexes once every three days for 6 months. After 6 months, the lightening and whitening effects were examined. In addition, the appearance of the cosmetic pack compositions upon coating was evaluated in the same manner as in Examples 2. The results are shown in Table 9.

TABLE 9

| | Lightening and whitening effects | | | | Appearance upon coating |
| --- | --- | --- | --- | --- | --- |
| Results | Remarkably effective | Effective | Slightly Effective | Ineffective | |
| Example 5 | 1 | 4 | 4 | 1 | A |
| Comparative Example 5 | 0 | 2 | 3 | 5 | C |

As is appreciated from Table 9, the pack composition of Example 5 of the present invention in which the ellagic acid-based compound having an average particle diameter of 0.2 μm and containing particles having a particle diameter of not more than 1 μm in an amount of 98% by weight was used, had more remarkable lightening and whitening effects, as compared to the composition of Comparative Example 5 containing non-pulverized ellagic acid-based compound. Incidentally, during and after the 6-week use of the pack composition according to the present invention, there was caused no abnormality on the skin to which the composition was applied.

In addition, the composition obtained in Example 5 of the present invention was more excellent in appearance upon coating than that of Comparative Example 6.

As described above, in accordance with the present invention, since the composition for external application incorporates therein the ellagic acid-based compound or the alkali metal salt thereof useful as lightening and whitening agent which has an average particle diameter of not more than 50 μm and contains particles having a particle diameter of not more than 70 μm in an amount of not less than 70% by weight, it is possible to provide a composition having a high percutaneous absorption property and extremely excellent lightening and whitening effects.

Further, if the particulate ellagic acid-based compound or the alkali metal salt thereof having an average particle diameter of not more than 10 μm and containing particles having a particle diameter of not more than 30 μm in an amount of not less than 70% by weight is used, the aforementioned property and effects can be further improved. Furthermore, if the particulate ellagic acid-based compound or the alkali metal salt thereof having an average particle diameter of not more than 1 μm and containing particles having a particle diameter of not more than 3 μm in an amount of not less than 70% by weight is used, the aforementioned property and effects can be still further improved.

Also, the composition for external application according to the present invention is excellent in appearance upon coating.

Accordingly, the composition for external application in which the afore-mentioned ellagic acid-based compound or the alkali metal salt thereof according to the present invention is blended, is useful as a base for various composition systems such as aqueous system, solubilized system, emulsifiable system, powder-dispersed system, water/oil two-layer system or water/oil/powder three-layer system. Further, the composition for external application according to the present invention is suitably applicable in various configurations to basic cosmetics such as creams, milky lotions, face lotions or toilet water, make-up cosmetics such as lipsticks or foundations, jelly-like agents, drugs or quasi-drugs such as unguents, or the like.

What is claimed is:

1. A composition for external application, comprising:

at least one particulate material selected from the group consisting of (a) an ellagic acid-based compound of the general formula (I):

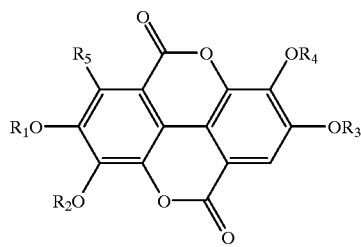
(I)

wherein $R^1$, $R^2$, $R^3$ and $R^4$ are the same or different and are independently hydrogen, an alkyl group having 1 to 20 carbon atoms, an acyl group having 1 to 20 carbon atoms, a polyoxyalkylene group of the formula: $-(C_mH_{2m}-O)_n-H$ where m is an integer of 2 or 3 and n is an integer of not less than 1, or a sugar residue of the formula (II):

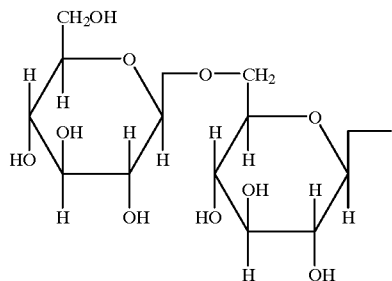
(II)

wherein $R^5$ is hydrogen, a hydroxyl group or an alkoxy group having 1 to 8 carbon atoms, and (b) an alkali metal salt of the ellagic acid- based compound, said particulate material having an average particle diameter of not more than 50 μm and containing particles having a particle diameter of not more than 70 μm in an amount of not less than 70% by weight based on the weight of the particulate material; and at least one alcohol selected from the group consisting of ethanol, propylene glycol, dipropylene glycol, glycerol and polyvinyl alcohol.

2. A composition according to claim 1, wherein said particulate material has an average particle diameter of not more than 10 μm and contains particles having a particle diameter of not more than 30 μm in an amount of not less than 70% by weight based on the weight of the particulate material.

3. A composition according to claim 1 additionally comprising water as a major portion of the composition.

4. A composition according to claim 1 wherein said particulate material is 0.001 to 30% by weight, based on the total weight of the composition.

5. A composition according to claim 4 additionally comprising water as a major portion of the composition.

6. A composition according to claim 1 wherein said particulate material is 0.05 to 10% by weight, based on the total weight of the composition.

7. A composition according to claim 6 additionally comprising water as a major portion of the composition.

8. A composition according to claim 1 wherein said particulate material is ellagic acid or an alkali metal salt thereof.

* * * * *